(12) United States Patent
Ali et al.

(10) Patent No.: US 11,384,077 B2
(45) Date of Patent: Jul. 12, 2022

(54) SOLID STATE FORM OF VALBENAZINE

(71) Applicant: ASSIA CHEMICAL INDUSTRIES LTD., Petach Tikva (IL)

(72) Inventors: Khaled Haj Ali, Tayibe (IL); Marina Yarovoy, Rosh-HaAyin (IL); Jonathan Enav, Bnei-Brak (IL)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 102 days.

(21) Appl. No.: 16/764,936

(22) PCT Filed: Nov. 21, 2018

(86) PCT No.: PCT/US2018/062211
§ 371 (c)(1),
(2) Date: May 18, 2020

(87) PCT Pub. No.: WO2019/104141
PCT Pub. Date: May 31, 2019

(65) Prior Publication Data
US 2020/0347047 A1    Nov. 5, 2020

Related U.S. Application Data

(60) Provisional application No. 62/589,791, filed on Nov. 22, 2017.

(51) Int. Cl.
*C07D 455/06*    (2006.01)
*A61K 9/00*    (2006.01)
*A61K 9/20*    (2006.01)
*A61K 9/48*    (2006.01)

(52) U.S. Cl.
CPC .......... *C07D 455/06* (2013.01); *A61K 9/0053* (2013.01); *A61K 9/20* (2013.01); *A61K 9/48* (2013.01); *C07B 2200/13* (2013.01)

(58) Field of Classification Search
CPC .. C07D 455/06; C07B 2200/13; C07C 309/30
See application file for complete search history.

(56) References Cited

U.S. PATENT DOCUMENTS

2017/0183346 A1    6/2017    McGee et al.

FOREIGN PATENT DOCUMENTS

| WO | 2017075340 A1 | 5/2017 |
| WO | 2018067945 A1 | 4/2018 |

OTHER PUBLICATIONS

International Search Report and Written Opinion of the International Searching Authority issued in corresponding Appl. No. PCT/US2018/062211 dated Feb. 4, 2019 (14 pages).

*Primary Examiner* — Noble E Jarrell
(74) *Attorney, Agent, or Firm* — Carter, DeLuca & Farrell LLP

(57) ABSTRACT

Salts and solid state forms of Valbenazine, including Valbenazine ditosylate, processes for preparation thereof, pharmaceutical compositions thereof, and uses thereof are disclosed.

20 Claims, 2 Drawing Sheets

Figure 1: An X-ray powder diffractogram (XRPD) of form T13 of Valbenazine ditosylate
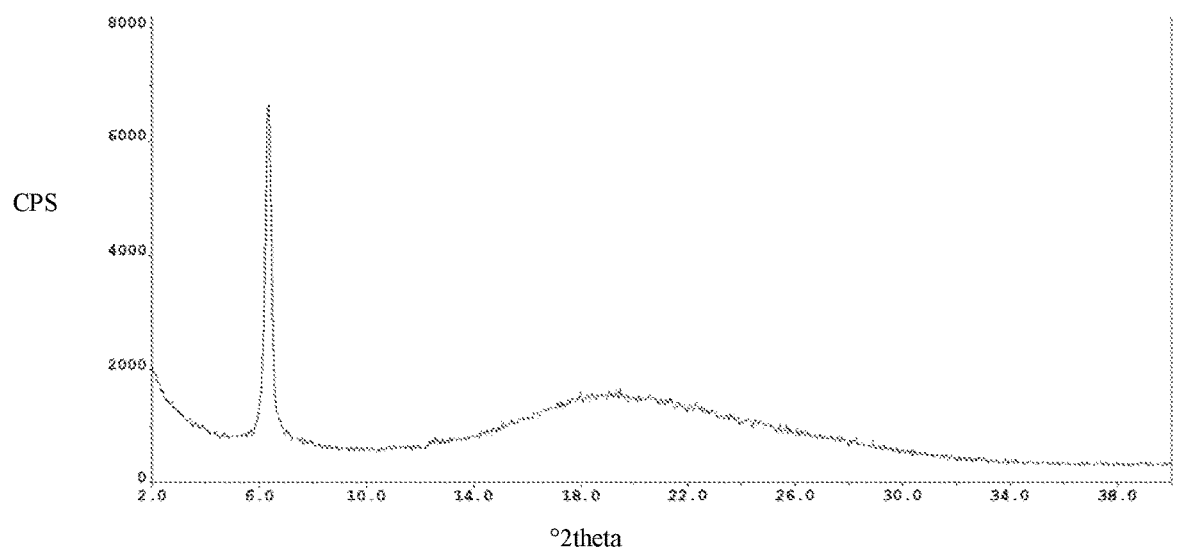

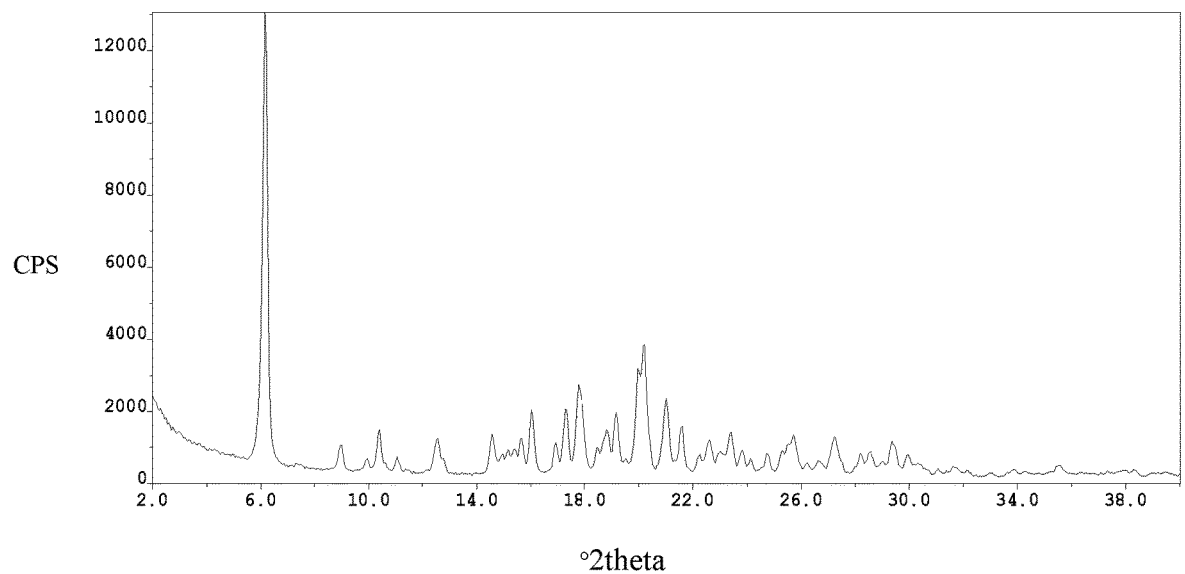
Figure 2: An X-ray powder diffractogram (XRPD) of form T3 of Valbenazine ditosylate

SOLID STATE FORM OF VALBENAZINE

CROSS REFERENCE TO RELATED APPLICATIONS

This application is a National Stage Application of, and claims priority to and the benefit of, International Patent Application No. PCT/US2018/062211 filed on Nov. 21, 2018, which, in turn, claims the benefit of, and priority to, U.S. Provisional Application No. 62/589,791 filed Nov. 22, 2017, the entire disclosures of each of which are incorporated by reference herein.

FIELD OF THE INVENTION

The present disclosure relates to a solid state form of Valbenazine ditosylate, processes for preparation thereof, and pharmaceutical compositions thereof.

BACKGROUND OF THE INVENTION

Valbenazine has the chemical name (2R,3R,11bR)-3-isobutyl-9,10-dimethoxy-1,3,4,6,7,11b-hexahydro-2H-pyrido[2,1-a] isoquinolin-2-yl L-valinate.

Valbenazine has the following chemical structure:

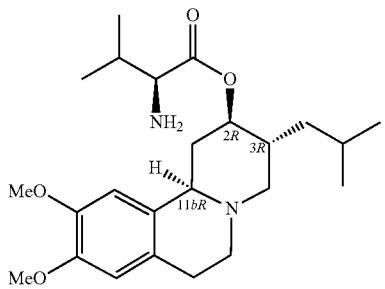 [SMILES: COc1cc2c(cc1OC)[C@H]1C[C@@H](OC(=O)[C@@H](N)C(C)C)[C@H](CC(C)C)CN1CC2]

Valbenazine is an inhibitor of vesicular monoamine transporter 2 (VMAT2) and is being developed by Neurocrine Bioscience for the treatment of a variety of central nervous system disorders, particularly involuntary hyperkinetic movement disorders such as drug-induced tardive dyskinesia and Tourette's syndrome. In the US, Valbenazine was approved for the treatment of tardive dyskinesia (TD) and is marketed under the name INGREZZA®.

Valbenazine is disclosed in U.S. Pat. No. 8,039,627. Valbenazine salts and polymorphs thereof are disclosed in WO 2017/075340. Crystalline Forms of Valbenazine salts have also been disclosed in WO2018/153632 and in our co-pending application WO 2018/067945.

Polymorphism, the occurrence of different crystal forms, is a property of some molecules and molecular complexes. A single compound, like Valbenazine, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}$C—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for additional solid state forms (including solvated forms or salts) of Valbenazine.

SUMMARY OF THE INVENTION

The present disclosure relates to a solid state form of Valbenazine ditosylate, processes for preparation thereof, and pharmaceutical compositions including this solid state form.

The present disclosure also provides uses of the solid state form of Valbenazine ditosylate for preparing other solid state forms of Valbenazine, Valbenazine salts, and solid state forms thereof.

The present disclosure also provides solid state form of Valbenazine ditosylate of the present disclosure for uses in the preparation of other solid state forms of Valbenazine, Valbenazine salts, and solid state forms thereof.

In another embodiment, the present disclosure encompasses the described solid state form of Valbenazine ditosylate for use in the preparation of pharmaceutical compositions and/or formulations, optionally for the treatment of a variety of central nervous system disorders, including involuntary hyperkinetic movement disorders such as drug-induced tardive dyskinesia and Tourette's syndrome.

In another embodiment, the present disclosure encompasses uses of the described solid state form of Valbenazine ditosylate for the preparation of pharmaceutical compositions and/or formulations.

The present disclosure further provides pharmaceutical compositions including the solid state form of Valbenazine ditosylate according to the present disclosure.

In yet another embodiment, the present disclosure encompasses pharmaceutical formulations including the described solid state form of Valbenazine ditosylate and at least one pharmaceutically acceptable excipient.

The present disclosure encompasses processes to prepare said pharmaceutical formulations of Valbenazine ditosylate including combining the described solid state form and at least one pharmaceutically acceptable excipient.

The solid state form defined herein as well as the pharmaceutical compositions or formulations of the solid state form of Valbenazine ditosylate can be used as medicaments, such as for the treatment of a variety of central nervous system disorders, including involuntary hyperkinetic movement disorders such as drug-induced tardive dyskinesia and Tourette's syndrome.

The present disclosure also provides methods of treating of a variety of central nervous system disorders, including involuntary hyperkinetic movement disorders such as drug-induced tardive dyskinesia and Tourette's syndrome, by administering a therapeutically effective amount of the solid state form of Valbenazine ditosylate of the present disclosure, or at least one of the herein described pharmaceutical compositions or formulations, to a subject suffering from of a central nervous system disorders, including involuntary hyperkinetic movement disorders such as drug-induced tardive dyskinesia and Tourette's syndrome, or otherwise in need of the treatment.

The present disclosure also provides uses of the solid state form of Valbenazine ditsosylate of the present disclosure, or at least one of the above pharmaceutical compositions or formulations, for the manufacture of medicaments for treating central nervous system disorders, including involuntary hyperkinetic movement disorders such as drug-induced tardive dyskinesia and Tourette's syndrome.

BRIEF DESCRIPTION OF THE FIGURES

FIG. 1 shows an X-ray powder diffractogram (XRPD) of form T13 of Valbenazine ditosylate.

FIG. 2 shows an X-ray powder diffractogram (XRPD) of form T3 of Valbenazine ditosylate.

DETAILED DESCRIPTION OF THE INVENTION

The present disclosure relates to a solid state form of Valbenazine ditosylate, processes for preparation thereof, and pharmaceutical compositions including this solid state form. The disclosure also relates to the conversion of the described solid state form of Valbenazine ditosylate to other solid state forms of Valbenazine, Valbenazine salts, and their solid state forms thereof.

The solid state form of Valbenazine ditsoylate according to the present disclosure may have advantageous properties such as at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Valbenazine referred to herein as being characterized by graphical data "as depicted in" a Figure will thus be understood to include any crystal forms of the Valbenazine, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or 0% of any other forms of the subject compound as measured, for example, by XRPD. Thus, the solid state form of Valbenazine described herein as substantially free of any other solid state forms would be understood to contain greater than about 80% (w/w), greater than about 90% (w/w), greater than about 95% (w/w), greater than about 98% (w/w), greater than about 99% (w/w), or 100% of the subject solid state form of Valbenazine. Accordingly, in some embodiments of the disclosure, the described solid state forms of Valbenazine may contain from about 1% to about 20% (w/w), from about 5% to about 20% (w/w), or from about 5% to about 10% (w/w) of one or more other solid state forms of the same Valbenazine.

As used herein, unless stated otherwise, XRPD peaks reported herein are optionally measured using CuK$_\alpha$ radiation, $\lambda=1.5418$ Å.

As used herein, the term "isolated" in reference to solid state forms of Valbenazine of the present disclosure corresponds to solid state form of Valbenazine that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein, the term "reduced pressure" refers to a pressure of about 10 mbar to about 50 mbar.

The present disclosure provides a solid state form of Valbenazine ditosylate designated as Form T13. The Form T13 of Valbenazine ditosylate can be characterized by data selected from one or more of the following: an XRPD pattern having a peak at 6.3 degrees 2-theta±0.2 degrees 2-theta; an XRPD pattern as depicted in FIG. 1; and combinations of these data. Solid state Form T13 may be further characterized by an XRPD pattern having a peak at 6.3 degrees 2-theta±0.2 degrees 2-theta and a broad peak between 14 and 26 2-theta±0.2 degrees 2-theta. Solid state Form T13 may be further characterized by an XRPD pattern having a peak at 6.3 degrees 2-theta±0.2 degrees 2-theta and a broad peak between 16 to 24 2-theta±0.2 degrees 2-theta.

Solid state Form T13 may be further characterized by an XRPD pattern having a peak at 6.3 degrees 2-theta±0.2 degrees 2-theta and a broad peak having a maximum between 18 to 21 2-theta±0.2 degrees 2-theta. Solid state Form T13 may be further characterized by an XRPD pattern having a peak at 6.3 degrees 2-theta±0.2 degrees 2-theta and a broad peak having a maximum between 19 to 20 2-theta±0.2 degrees 2-theta.

Form T13 of Valbenazine ditosylate is polymorphically and chemically stable.

Form T13 of Valbenazine ditosylate is substantially free of residual solvents. In embodiments, Form T13 of Valbenazine ditosylate contains less than 1% (w/w), in some embodiments less than 0.5% (w/w), in other embodiments less than 0.1% (w/w), and in yet other embodiments less than 0.052% (w/w) organic solvent.

Form T13 of Valbenazine according to any one or more of the above embodiments may be substantially free of any other solid state or polymorphic forms of Valbenazine ditosylate.

The present disclosure also provides the solid state form of Valbenazine ditosylate of the present disclosure for use in the preparation of other solid state forms of Valbenazine, Valbenazine salts and their solid state forms thereof.

The present disclosure further provides a process for preparing a solid state form of Valbenazine ditosylate which includes desolvating a solvated form of Valbenazine ditosylate with an organic solvent, in embodiments wherein the solvated form of Valbenazine ditosylate is Form T3, in other embodiments wherein the solvated form of Valbenazine ditosylate Form T3 is a methyl-tetrahydrofuran (Me-THF) solvate, a tetrahydrofuran (THF) solvate, a methylethyl ketone (MEK) solvate, or a 1,4-dioxane solvate. In embodiments, the solvated form of Valbenazine ditosylate is Form T3 Me-THF solvate. The desolvation may be carried out by drying of the solvated Form of Valbenazine ditosylate under conditions suitable for removal of the organic solvent from the solvated form of Valbenazine ditosylate. Removal of the organic solvent from the solvated form of Valbenazine ditosylate preferably reduces the organic solvent to less than 1% (w/w), in embodiments less than 0.5% (w/w), in embodiments less than 0.1% (w/w), in other embodiments less than 0.052% (w/w) organic solvent.

Desolvation may be carried out at temperatures between 70° C. to 100° C., in embodiments at temperatures between 75° C. to 90° C. and applying a vacuum. The vacuum applied may be between 1 to 100 mbar, in embodiments at a pressure of between 5-50 mbar. Desolvation may be carried out for 24-300 hours, in embodiments 60-250 hours, in other embodiments 100-150 hours.

Solvated Form T3 of Valbenazine can be prepared by a one-pot process for the preparation of Valbenazine ditosylate starting from (R,R,R)-Dihydrotetrabenazine according to scheme 1:

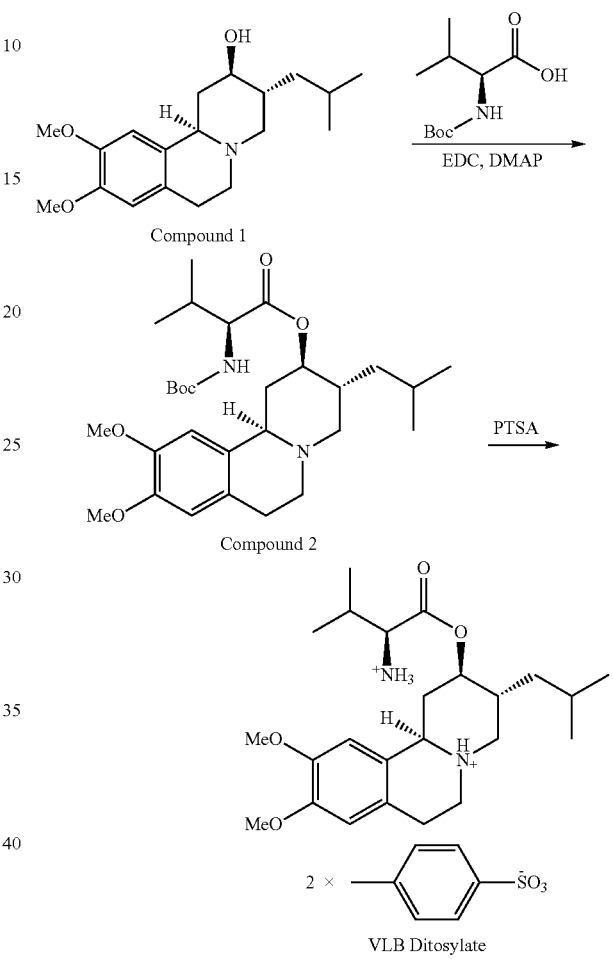

The process includes
a) reacting (R,R,R)-Dihydrotetrabenazine (Compound 1) with amine-protected Valine amino acid in a suitable solvent in the presence of a coupling agent in order to obtain amino-protected Valbenazine (Compound 2),
b) removal of the amine protecting group from Compound 2 with p-toluenesulfonic acid to obtain Valbenazine ditosylate salt, and
c) precipitation of Valbenazine ditosylate as Form T3 of Valbenazine ditosylate. The process can be followed by desolvation of solvated Form T3 of Valbenazine ditosylate. The Form T3 may be desolvated to obtain Valbenazine ditosylate Form T13.

(R,R,R)-Dihydrotetrabenazine can be prepared according to methods disclosed in, for example, U.S. Pat. No. 8,039,627 or WO 2018/067945. The amino group of the amine-protected Valine amino acid can be protected by protecting groups such as Boc (tert-butyloxycarbonyl), Trytil, Ddz, Bpoc, Nps or MTT protecting groups. Any suitable protecting groups for amines can be used (see, e.g., Greene's Protective Groups in Organic Synthesis, Fifth Edition (2014), P. G. M. Wuts, Wiley). As coupling agents, reagents such as DCC (N,N'-dicyclohexylcarbodiimide), EDC (1-Ethyl-3-(3-dimethylaminopropyl)carbodiimide) or DIC (N,N-Diisopropylcarbodiimide) can be used, in embodiments with the addition of an appropriate additive such as, but not limited to, NHS (N-hydroxysuccinimide), HOBt (Hydroxybenzotriazole) or DMAP (4-Dimethylaminopyridine). The reaction can be conducted in a range of temperatures from 0° C. to 100° C., in embodiments from 10° C. to 70° C., in other embodiments from 20° C. to 30° C., in a suitable solvent, in embodiments toluene. In some embodiments, the amine protecting group is removable by p-toluenesulfonic acid in order to directly obtain Valbenazine ditosylate.

Valbenazine ditosylate Form T3 Me-THF solvate can be precipitated from the reaction mixture by addition of Me-THF. Valbenazine ditosylate Form T3 Me-THF solvate may contain 4.5%-2% of Me-THF, in embodiments 4%-2.5% Me-THF. Valbenazine ditosylate Form T3 can be characterized by data selected from one or more of the following: an XRPD pattern having peaks at 6.1, 9.0, 14.6, 17.3 and 21.6 degrees 2-theta±0.2 degrees 2-theta; an XRPD pattern as depicted in FIG. 2; and combinations of these data. Crystalline Form T3 of Valbenazine ditosylate may be further characterized by the XRPD pattern having peaks at 6.1, 9.0, 14.6, 17.3 and 21.6 degrees 2-theta±0.2 degrees 2-theta, and also having one, two, three, four or five additional peaks selected from 10.4, 16.0, 17.8, 20.2 and 21.0 degrees 2-theta±0.2 degrees 2-theta. Valbenazine ditosylate Form T3 Me-THF solvate as described in any of the above embodiments may contain 4.5%-2% of Me-THF, in embodiments 4%-2.5% Me-THF. Form T3 of Valbenazine ditosylate is also disclosed in WO 2018/067945, and may alternatively be prepared by the examples disclosed therein.

Valbenazine ditosylate Form T3 Me-THF solvate can be further converted to Valbenazine ditosylate Form T13 by desolvation according to any embodiment of the desolvation process of the present disclosure.

The disclosed process shows high yield and results in a pure final product Valbenazine ditosylate without further recrystallization steps.

The present disclosure further encompasses a solid state form of Valbenazine ditosylate which is obtainable by any aspect or embodiment of the processes described herein. The solid state form of Valbenazine ditosylate may be characterized as Form T13 according to any aspect or embodiment of the disclosure as described herein.

The present disclosure further encompasses processes for preparing Valbenazine salts or solid state forms thereof. The process comprises preparing the solid state form of the present disclosure, and converting it to another Valbenazine salt. The conversion can be done, for example, by processes including reacting the obtained Valbenazine solid state form with an appropriate base to obtain the corresponding base-addition salt.

In another embodiment, the present disclosure encompasses the above described solid state form of Valbenazine ditosylate for use in the preparation of pharmaceutical compositions and/or formulations, optionally for the treatment of central nervous system disorders, including involuntary hyperkinetic movement disorders such as drug-induced tardive dyskinesia and Tourette's syndrome.

In another embodiment, the present disclosure encompasses the use of the above described solid state form of Valbenazine ditosylate for the preparation of pharmaceutical compositions and/or formulations. The present disclosure also provides the solid state form of Valbenazine ditosylate of the present disclosure for use in the preparation of pharmaceutical compositions and/or formulations.

The present disclosure further provides pharmaceutical compositions including the solid state form of Valbenazine ditosylate according to the present disclosure.

In yet another embodiment, the present disclosure encompasses pharmaceutical formulations including the above described solid state form of Valbenazine ditosylate and at least one pharmaceutically acceptable excipient.

The present disclosure encompasses processes to prepare said formulations of Valbenazine ditosylate including combining the above solid state form of Valbenazine ditosylate and at least one pharmaceutically acceptable excipient.

The solid state form of Valbenazine ditosylate as defined herein, as well as the pharmaceutical compositions or formulations thereof can be used as medicaments, in embodiments for the treatment of central nervous system disorders, such as involuntary hyperkinetic movement disorders such as drug-induced tardive dyskinesia and Tourette's syndrome.

The present disclosure also provides methods of treating central nervous system disorders, in embodiments involuntary hyperkinetic movement disorders such as drug-induced tardive dyskinesia and Tourette's syndrome, including administering a therapeutically effective amount of the solid state form of Valbenazine ditosylate in the present disclosure, or at least one of the above pharmaceutical compositions or formulations, to a subject suffering from central nervous system disorders, including involuntary hyperkinetic movement disorders such as drug-induced tardive dyskinesia and Tourette's syndrome, or otherwise in need of the treatment.

The present disclosure also provides use of the solid state form of Valbenazine ditosylate of the present disclosure, or at least one of the above pharmaceutical compositions or formulations for the manufacture of a medicament for treating central nervous system disorders, including involuntary hyperkinetic movement disorders such as drug-induced tardive dyskinesia and Tourette's syndrome.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-ray Powder Diffraction Method:

The analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min.

Prior to analysis, the samples were gently ground using a mortar and pestle to obtain a fine powder. The ground sample was adjusted into a cavity of the sample holder and the surface of the sample was smoothed using a cover glass.

EXAMPLES

Valbenazine starting material can be prepared according to methods within the purview of the skilled artisan (for example, those disclosed in U.S. Pat. No. 8,039,627).

Example 1 Preparation of Valbenazine Ditosylate Form T13

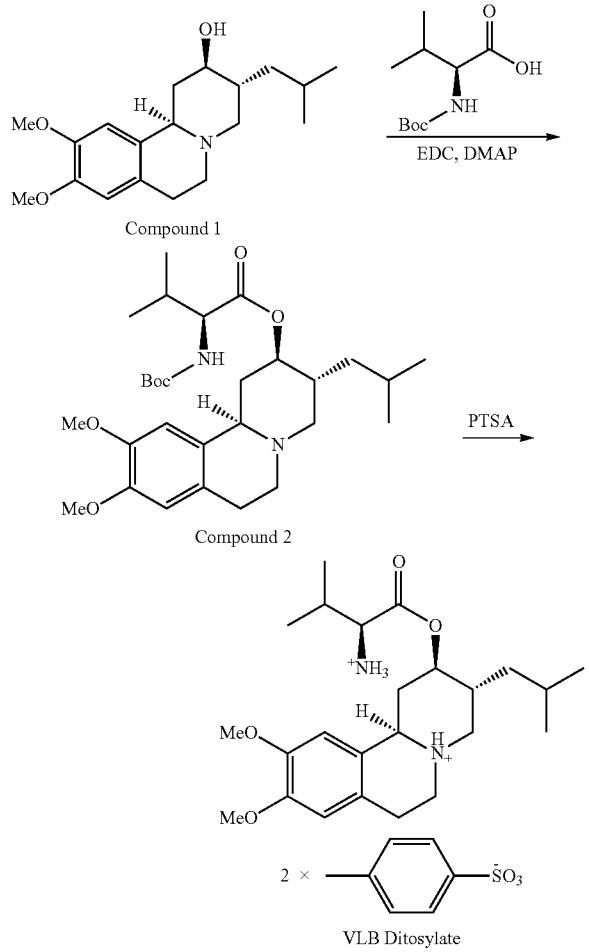

Synthesis of compound Valbenazine ditosylate (VLB Ditosylate)

(2R, 3R, 11bR)-3-isobutyl-9,10-dimethoxy-1,3,4,6,7,11b-hexahydro-2H-pyrido[2,1-a]isoquinolin-2-ol (Compound 1; 225 grams, 0.7 mol, 1 eq), Boc-Val-OH (229.7 grams, 1.06 mol, 1.5 eq), 4-(dimethylamino)pyridine (DMAP; 43.1 grams, 0.35 mol., 0.5 eq) was dissolved in toluene (450 ml, 2 vol) and DMA (225 ml, 1 vol) at room temperature. Then N-(3-dimethylaminoppropyl)-N'-ethylcarbodiimide hydrochloride (EDC-HCl; 297.3 grams, 1.55 mol, 2.2 eq) and additional amount of toluene (225 ml, 1 vol) were added and the reaction mixture was stirred at room temperature for 3.5 hours. Upon completion, the reaction mixture was washed with water (2250 ml*2, 10 vol vs. Compound 1 v/w). P-toluenesulfonic acid (PTSA; 938.6 grams, 4.93 mol,7 eq) and water (225 ml, 1 vol) were added to the organic phase and the reaction mixture was stirred at room temperature for 17.5 hours. Upon completion, Me-THF (4500 ml, 20 vol vs Compound 1) was added. The solution was cooled to 18° C. and first precipitations were observed. Then the mixture was heated to 38° C. and stirred for 1 hour. The obtained slurry was cooled to −5° C. during 6 hours and stirred at −5° C. for 16 hours.

The product Valbenazine ditosylate was collected by vacuum filtration, washed with Me-THF (2*450 ml) and dried in a vacuum oven at 50° C. for 20 hours to obtain valbenazine ditosylate Form T3 (420 g, 78% yield, 99.86% purity).

4 gr of the obtained product was dried in vacuum oven at 90° C. for 120 hours to obtain Valbenazine ditosylate Form T13 as depicted in FIG. 1.

The invention claimed is:

1. Solid state form of Valbenazine ditosylate designated as Form T13, characterized by data selected from one or more of the following:
  (a) a XRPD pattern consisting essentially of a peak at 6.3 degrees 2-theta±0.2 degrees 2-theta and a broad peak between 13.0 to 34.0 2-theta±0.2 degrees 2-theta; or
  (b) an XRPD pattern substantially as depicted in FIG. 1; and
  (c) combinations of these data.

2. The solid state form of Valbenazine ditosylate according to claim 1, which is characterized by a XRPD pattern consisting essentially of a peak at 6.3 degrees 2-theta±0.2 degrees 2-theta and a broad peak between 16.0 to 24.0 2-theta±0.2 degrees 2-theta.

3. The solid state form of Valbenazine ditosylate according to claim 1, wherein the broad peak exhibits a maximum at 18.0 to 21.0 2-theta±0.2 degrees.

4. The solid state form of Valbenazine ditosylate according to claim 1, wherein the broad peak exhibits a maximum at 19.0 to 20.0 2-theta±0.2 degrees 2-theta.

5. The solid state form of Valbenazine ditosylate according to claim 1, which is substantially free of organic solvents.

6. The solid state form of Valbenazine ditosylate according to claim 1 which is substantially free of any other solid state form of Valbenazine ditosylate.

7. A process for preparing a solid state form of Valbenazine ditosylate comprising desolvating a solvated form of Valbenazine ditosylate with an organic solvent, wherein the solvated form of Valbenazine ditosylate is Form T3.

8. The process according to claim 7, wherein Form T3 is characterized by data selected from one or more of the following: an XRPD pattern having peaks at 6.1, 9.0, 14.6, 17.3 and 21.6 degrees 2-theta±0.2 degrees 2-theta; or an XRPD pattern as depicted in FIG. 2; or a combination thereof.

9. The process according to claim 7, wherein Form T3 is further characterized by the XRPD pattern having peaks at 6.1, 9.0, 14.6, 17.3 and 21.6 degrees 2-theta±0.2 degrees 2-theta, and also having one, two, three, four or five additional peaks selected from 10.4, 16.0, 17.8, 20.2 and 21.0 degrees 2-theta±0.2 degrees 2-theta.

10. The process according to claim 7, wherein the solvated form or Form T3 of Valbenazine ditosylate is a methyl-tetrahydrofuran (Me-THF) solvate, a tetrahydrofuran (THF) solvate, a methylethyl ketone (MEK) solvate, or a 1,4-dioxane solvate.

11. The process according to claim 7, wherein the solvated form of Valbenazine ditosylate is Form T3 Me-THF solvate, and wherein the desolvating reduces the organic solvent of the solvate to less than 1% (w/w) organic solvent.

12. The process according to claim 7, wherein the desolvating comprises heating the solvated form of Valbenazine ditosylate at a temperature of 60-120° C., more preferably 70 to 110° C.

13. The process according to claim 12, wherein the heating is conducted under reduced pressure, at a pressure of 1-100 mbar.

14. The process according to claim 7, further comprising combining the solid state form of Valbenazine ditosylate with a pharmaceutically acceptable excipient to form a pharmaceutical composition or formulation.

15. The process according to claim 7, wherein the solid state Form T3 is prepared by a one-pot process comprising:
   a) reacting (R,R,R)-Dihydrotetrabenazine (Compound 1) with amine-protected Valine amino acid in a suitable solvent in the presence of a coupling agent to obtain amino-protected Valbenazine (Compound 2);
   b) removal of the amine protecting group from Compound 2 with p-toluenesulfonic acid to obtain Valbenazine ditosylate salt;
   c) precipitation of Valbenazine ditosylate as Form T3 of Valbenazine ditosylate.

16. The process according to claim 15, wherein Valbenazine ditosylate Form T3 is precipitated by the addition of Me-THF to the reaction mixture and isolation of Valbenazine ditosylate Form T3 Me-THF solvate.

17. A medicament comprising the solid state form of Valbenazine ditosylate according to claim 1.

18. A pharmaceutical composition or formulation comprising the solid state form of Valbenazine ditosylate according to claim 1.

19. A pharmaceutical composition or formulation according to claim 18 comprising at least one pharmaceutically acceptable excipient, wherein the pharmaceutical composition or formulation is for oral administration.

20. A method for treating involuntary hyperkinetic movement disorders, drug-induced tardive dyskinesia or Tourette's syndrome, comprising administering the medicament of claim 17 to a patient in need of treatment.

* * * * *